United States Patent [19]

Bonifaz et al.

[11] Patent Number: 5,045,297

[45] Date of Patent: Sep. 3, 1991

[54] SELECTIVE OXIDATION OF CARBON MONOXIDE IN A MIXTURE

[76] Inventors: Christobal Bonifaz, Conway, Mass.; David R. Corbin, West Chester, Pa.

[73] Assignee: E. I. duPont de Nemours and Company, Wilmington, Del.

[21] Appl. No.: 341,859

[22] Filed: Mar. 31, 1989

[51] Int. Cl.$^5$ ............................................. C01B 31/20
[52] U.S. Cl. .................................. 423/437; 423/247; 423/415 R; 502/262
[58] Field of Search ................ 423/247, 437, 415 R; 502/262; 549/262

[56] References Cited

U.S. PATENT DOCUMENTS

| | | | |
|---|---|---|---|
| 2,756,121 | 7/1956 | Grimes | 423/437 |
| 3,141,739 | 7/1964 | Ohlgren et al. | 423/437 |
| 3,216,783 | 11/1965 | Cohn | 23/2 |
| 3,373,110 | 3/1968 | Chen | 252/455 |
| 3,790,662 | 2/1974 | Lloyd et al. | 423/437 |
| 4,046,956 | 9/1977 | Fanciullo | 429/20 |
| 4,222,856 | 9/1980 | Hansel et al. | 423/437 |
| 4,238,460 | 12/1980 | Aiken et al. | 549/262 |
| 4,292,288 | 9/1981 | Gladrow | 423/437 |
| 4,400,364 | 8/1983 | Storm | 423/247 |
| 4,608,357 | 8/1986 | Silverman et al. | 423/247 |
| 4,623,637 | 11/1986 | von der Smissen | 423/247 |

FOREIGN PATENT DOCUMENTS

| | | | |
|---|---|---|---|
| 189261 | 7/1986 | European Pat. Off. | 549/262 |
| 2019839 | 11/1979 | United Kingdom | 549/262 |

OTHER PUBLICATIONS

Chen et al., "Kinetics and Catalysis", Chemical Engineering Progress Symposium Series, vol. 63, No. 73, pp. 86-89 (1967).

Benesi et al., J. Catal. 10, 328-335 (1968).

*Primary Examiner*—Robert Kunemund

[57] ABSTRACT

A process for the selective oxidation of carbon monoxide from a mixture of organics over a supported platinum or palladium catalyst.

19 Claims, No Drawings

SELECTIVE OXIDATION OF CARBON MONOXIDE IN A MIXTURE

BACKGROUND OF THE INVENTION

1. Field of the Invention

This invention relates to a process for the removal of carbon monoxide from a mixture of organics by its selective oxidation. The process can be used for the oxidation of carbon monoxide from a hydrocarbon and/or a partially oxidized hydrocarbon mixture, such as the mixture resulting from the gas phase catalytic oxidation of n-butane to maleic anhydride with air or oxygen. Significant amounts of carbon monoxide are produced as the by-product of that oxidation (see Triverdi, B. C. and Culbertson, B. M., "Maleic Anhydride", Plenum, N.Y. (1982), Chapter 2).

In commercial processes for the production of maleic anhydride from n-butane, to maximize the overall conversion of n-butane to maleic anhydride, recirculation of the product stream is often necessary. In a typical situation, unreacted n-butane will be separated from the maleic anhydride and is recycled along with other gases to the reactor. Without the separation of carbon monoxide from the product stream, there could be a build up of carbon monoxide in the recirculation process, resulting in a significant explosion hazard. It is useful, therefore, to eliminate the carbon monoxide that occurs in the butane to maleic anhydride reaction, while avoiding butane or maleic anhydride losses to undesirable oxidation products. This can be accomplished, either by eliminating the carbon monoxide at the reactor level by modifying the catalyst or by the elimination of CO in the product stream, by, for example, passing the product stream over an appropriate catalyst bed. The present process selectively removes CO from mixtures containing hydrocarbons and/or partially oxidized hydrocarbons (e.g. maleic anhydride), by passing the mixture over a catalyst composed of Pd or Pt on an inert silica or silica containing vanadium phosphate support at temperatures up to 500° C., in the presence of oxygen.

2. Description of the Prior Art

The prior art discloses numerous processes for the oxidation of carbon monoxide in the presence of hydrogen. However, some of these processes have resulted in concurrent oxidation of the other components of the mixture, causing loss of the desired product and a contaminated product.

U.S. Pat. No. 3,216,783 discloses the preferential, low temperature oxidation of carbon monoxide to carbon dioxide in admixture with a gas stream containing hydrogen, over a supported platinum catalyst. The process results in the preferential oxidation of carbon monoxide and the simultaneous reaction of oxygen with hydrogen to form water.

U.S. Pat. No. 4,400,364 discloses a process for the selective oxidation of carbon monoxide to carbon dioxide in the presence of methacrolein, over a catalyst system comprising specific aluminosilicates having pores no larger than 0.4-0.5 millimicrometers and having within the pores a noble metal or a base metal having the ability to catalyze carbon monoxide oxidation.

N. Y. Chen and P. B. Weisz, "Kinetics and Catalysis", Chemical Engineering Progress Symposium Series, Vol. 63, No. 73, pp. 86 to 89, (1967) disclose the shape-selective oxidation of carbon monoxide and butane, in separate streams over Pt/Na-A zeolite.

U.S. Pat. No. 3,373,110 discloses a process for the preparation of platinum metal containing aluminosilicates whose improved crystallinity are illustrated by catalytic oxidation tests.

Benesi, H. A.; Curtis, R. M.; Struder, H. P., J. Catal. 1968, 10, 328-335 disclose the preparation of supported platinum on silica.

SUMMARY OF THE INVENTION

The present invention provides a process for the selective oxidation of carbon monoxide in the presence of a hydrocarbon such as butane and/or partially oxidized hydrocarbons, such as maleic anhydride, over a catalyst composed of Pd or Pt deposited on a silica or on a silica containing vanadium phosphate support. The process can be conducted at temperatures up to 500° C. The preferred metal for use in the present process is Pd. The process of the present invention is useful for providing a product stream that is essentially free of carbon monoxide for recycling, as, for example, in a process for making maleic anhydride from butane.

DESCRIPTION OF THE PREFERRED EMBODIMENTS

This invention provides a process for the oxidation of carbon monoxide to carbon dioxide, in the presence of a hydrocarbon such as butane and/or a partially oxidized specie, such as maleic anhydride. The process involves contacting a gaseous mixture containing carbon monoxide, where such gaseous mixture optionally contains butane and maleic anhydride, with a catalyst composed of Pd or Pt, on a support composed of silica or a silica containing vanadium phosphate. If the metal is Pd, the preferred metal loading is greater than about $1.5 \times 10^{-4}$ wt. % but less than about $4.0 \times 10^{-4}$ wt. %. If the metal is Pt, the preferred loading is between about 0.005 and 0.0005 wt. %.

The reactor may be a fixed, fluid or riser bed type. CO removal from a stream containing CO, butane and maleic anhydride is by use of Pd or Pt on silica catalyst. Preferred for such a stream is Pd on a vanadium/phosphorous oxide (V/P/O) silica support. Preliminary treatment of the catalyst with hydrogen is recommended when the metal used is Pt. Reactions may be conducted at temperatures up to 500° C. However, the preferred reaction temperature range is 350°–450° C.

The vapor phase oxidation of n-butane to maleic anhydride can be carried out using conventional techniques, for example, in a fixed-bed reactor, by contacting an activated catalyst species with n-butane and oxygen, in appropriate concentrations. This is done in the presence of one or more diluent gases. Air provides a satisfactory source of oxygen, although synthetic mixtures of oxygen and such gases as nitrogen, argon, helium and water vapor may be used. A molar excess of oxygen is recommended.

It is preferred to carry out the oxidation of n-butane to maleic anhydride at a hydrocarbon concentration of about 1.5% in air (by volume) for a fixed bed type of operation. The oxidation may be carried out within a temperature range of 300° to 500° C., preferably within the 350° to 450° C. range. Operating pressures can range between 0.5 to 20 atmospheres (50 to 2000 kPa) but are preferably in the range of 1 to 7 atmospheres, and more preferably 2 to 4 atmospheres. Contact times can vary from 0.1 to 15.0 seconds, although 0.2–4.0 seconds have been found to be preferable.

EXPERIMENTS

Catalyst Preparation

Catalysts were prepared by contacting supports with dilute $NH_4OH$ solutions containing $(NH_3)_4Pd(NO_3)_2$ or $(NH_3)_4Pt(NO_3)_2$ at various salt concentrations:

Background Experiment 1—Pd/SiO$_2$

A sample of Pd/SiO$_2$ was prepared by contacting 10 g of silica gel (Davison Grade 952) with 150 mL $10^{-7}$M $(NH_3)_4Pd(NO_3)_2$ for 5 minutes with stirring. The mixture was filtered, washed, and dried. The calculated loading (weight %) of Pd assuming complete ion-exchange is 0.000016.

Background Experiment 2—Pd/SiO$_2$ 20 g of silica gel (Davison Grade 952) were contacted with 200 mL of a $NH_4OH:H_2O$ (1:3) solution of $1.67 \times 10^{-6}$M $(NH_3)_4Pd(NO_3)_2$ for 5 minutes with stirring. The mixture was filtered, washed, and dried. The calculated loading (weight %) of Pd assuming complete ion-exchange is 0.00018.

Background Experiment 3—Pd/SiO$_2$ 10 g of silica gel (Davison Grade 952) were contacted with 200 mL of a $NH_4OH:H_2O$ (1:3) solution of $1.67 \times 10^{-6}$M $(NH_3)_4Pd(NO_3)_2$ for 5 minutes with stirring. The mixture was filtered, washed, and dried. The calculated loading (weight %) of Pd assuming complete ion-exchange is 0.00036.

Background Experiment 4—Pd/SiO$_2$ 10 g of silica gel (Davison Grade 952) were contacted with 200 mL of a $NH_4OH:H_2O$ (1:3) solution of $5.0 \times 10^{-5}$M $(NH_3)_4Pd(NO_3)_2$ for 5 minutes with stirring. The mixture was filtered, washed, and dried. The calculated loading (weight %) of Pd assuming complete ion-exchange is 0.011.

Background Experiment 5—Pd/SiO$_2$ 20 g of silica gel (Davison Grade 952) were contacted with 200 mL of a $NH_4OH:H_2O$ (1:3) solution of 200 mL $5.0 \times 10^{-4}$M $(NH_3)_4Pd(NO_3)_2$ for 5 minutes with stirring. The mixture was filtered, washed, and dried. The calculated loading (weight %) of Pd complete ion-exchange is 0.11.

Background Experiment 6—Pt/SiO$_2$ 10 g of silica gel (Davison Grade 952) were contacted with 200 mL of a $NH_4OH:H_2O$ (~1:3) solution of $2.6 \times 10^{-4}$M $(NH_3)_4Pt(NO_3)_2$ for 5 minutes with stirring. The mixture was filtered, washed, and dried. The calculated loading (weight %) of Pt assuming complete ion-exchange is 0.1.

Background Experiment 7—Pt/SiO$_2$ 10 g of silica gel (Davison Grade 952) were contacted with 200 mL of a $NH_4OH:H_2O$ (~1:3) solution of $2.6 \times 10^{-5}$M $(NH_3)_4Pt(NO_3)_2$ for 5 minutes with stirring. The mixture has filtered, washed, and dried. The calculated loading (weight %) of Pt assuming complete ion-exchange is 0.01.

Background Experiment 8—Pt/SiO$_2$ 10 g of silica gel (Davison Grade 952) were contacted with 200 mL of a $NH_4OH:H_2O$ (~1:3) solution of $1.3 \times 10^{-5}$M $(NH_3)_4Pt(NO_3)_2$ for 5 minutes with stirring. The mixture was filtered, washed, and dried. The calculated loading (weight %) of Pt assuming complete ion-exchange is 0.005.

Background Experiment 9—Pt/SiO$_2$ 10 g of silica gel (Davison Grade 952) were contacted with 200 mL of a $NH_4OH:H_2O$ (~1:3) solution of $2.6 \times 10^{-6}$M $(NH_3)_4Pt(NO_3)_2$ for 5 minutes with stirring. The mixture was filtered, washed, and dried. The calculated loading (weight %) of Pt assuming complete ion-exchange is 0.001.

Background Experiment 10—Pt/SiO$_2$ 10 g of silica gel (Davison Grade 952) were contacted with 200 mL of a $NH_4OH:H_2O$ (~1:3) solution of $1.3 \times 10^{-6}$M $(NH_3)_4Pt(NO_3)_2$ for 5 minutes with stirring. The mixture was filtered, washed, and dried. The calculated loading (weight %) of Pt assuming complete ion-exchange is 0.0005.

Background Experiment 11—Pt/SiO$_2$ 10 g of silica gel (Davison Grade 952) were contacted with 200 mL of a $NH_4OH:H_2O$ (~1:3) solution of $2.6 \times 10^{-7}$M $(NH_3)_4Pt(NO_3)_2$ for 5 minutes with stirring. The mixture was filtered, washed, and dried. The calculated loading (weight %) of Pt assuming complete ion-exchange is 0.0001.

Background Experiment 12—Pt-A

A sample of Pt-A zeolite was prepared as follows: A solution containing 40.5 g $NaAlO_2$, 75 g NaOH, 900 mL $H_2O$, and 0.100 g $(NH_3)_4PtCl_2 \cdot H_2O$ was added to a solution containing 31.8 g $Na_2SiO_3 \cdot 5H_2O$, and 600 $H_2O$ at 90° C. The mixture was stirred until crystalline and then was filtered, washed, and dried.

Background Experiment 13—Pt-A

A sample of Pt-A zeolite was prepared as follows: A solution containing 40.5 g $NaAOl_2$, 75 g NaOH, 900 mL $H_2O$, and 0.050 g $(NH_3)_4PtCl_2 \cdot H_2O$ was added to a solution containing 31.8 g $Na_2SiO_3 \cdot 5H_2O$, and 600 $H_2O$ at 90° C. The mixture was stirred until crystalline and then was filtered, washed, and dried.

Background Experiment 14—Pt-A

A sample of Pt-A zeolite was prepared as follows: A solution containing 40.5 g $NaAlO_2$, 75 g NaOH, 900 mL $H_2O$, and 0.005 g $(NH_3)_4PtCl_2 \cdot H_2O$ was added to a solution containing 31.8 g $Na_2SiO_3 \cdot 5H_2O$, crystalline and then was filtered, washed, and dried.

Background Experiment 15—Pt-A

A sample of Pt-A zeolite was prepared as follows: A solution containing 40.5 g $NaAlO_2$, 75 g NaOH, 900 mL $H_2O$, and 0.001 g $(NH_3)_4PtCl_2 \cdot H_2O$ was added to a solution containing 31.8 g $Na_2SiO_3 \cdot 5H_2O$, and 600 $H_2O$ at 90° C. The mixture was stirred until crystalline and then was filtered, washed, and dried.

Background Experiment 16—V/P/O

From Example 1 of U.S. Pat. No. 4,677,084: The preparation comprises the following steps: synthesis of the V/P/O catalyst precursor, preparation of the 5 wt % SiO$_2$ solution of polysilicic acid (PSA), preparation and spray drying of the V/P/O precursor-PSA slurry, calcination and activation.

A V/P/O catalyst precursor containing a promoter comprised of 2 weight percent $SiO_2$ and 2.5 atom percent In was prepared following Example 1 of U.S. Pat. No. 4,371,702. A 15 gallon (5.68 L) crystallizer type kettle was charged with 3600 g of comminuted $V_2O_5$, 36 L of isobutyl alcohol and 3.6 L of benzyl alcohol. The liquids were stirred while the $V_2O_5$ was added. The mixture was heated at reflux for 14 h. 5400 g of 85% $H_3PO_4$ were added over a 2-h period at the rate of 45 mL/10 minutes. The mixture was heated at reflux for 20 h. The slurry was filtered and the filtrate was recycled, until it was clear. The solid was comminuted to a powder with particles of size 1 and 3 micrometers. 7068 g of V/P/O catalyst precursor was thus produced. A 5 wt % $SiO_2$ polysilicic acid solution was prepared by diluting 1014 g of JM grade sodium silicate solution (300 g $SiO_2$) with 4985 g of distilled water in an 8-L stainless steel beaker. The solution was stirred for a few minutes and then filtered through folded filter paper to give a clear water-like filtrate. This clear filtrate with pH of 11.3 was stirred vigorously while Dowex HCR-W2-H resin, a strongly acidic nuclear sulfonic acid cation exchanger supplied by Dow Chemical Company, was added to reduce the pH. When the pH was about 6.8, excess resin was added to reduce the PH below 5.5 rapidly, thus avoiding microgel formation. When the pH reached $3.0+/-0.1$, the resin was filtered off and the clear filtrate was used within an hour to prepare the V/P/O precursor-PSA slurry for spray drying. 4444 g of the 5 wt % $SiO_2$ PSA solution was added to a mixing bowl and with the mixer on low speed, 2000 g of V/P/O comminuted catalyst precursor was added in small portions over a period of 30-45 minutes. The resulting slurry, containing 34.48% solids (90% V/P/O catalyst precursor and 10% $SiO_2$), had a pH of $2.5+/-0.1$.

The slurry was spray dried at the rate of 150 mL/min with atomizer area pressure set at 8 psi (55.2 kPa) and a chamber temperature of $245°+/-5°$ C.

Background Experiment 17—Pd/V/P/O 20 g of V/P/O catalyst was prepared above in BE 16 was contacted with 300 mL of a $1.0\times10^{-7}$M solution of $(NH_3)_4Pd(NO_3)_2$ for 5 minutes with stirring. The slurry was filtered, washed, and dried. The calculated loading (weight %) of Pd assuming complete ion-exchange is 0.00018.

Background Comparative Experiment 1—Silicalite

A mixture of ethylsilicate (40%, 235 g), tetraethylammonium hydroxide (40%, 200 g), tetrapropylammonium bromide (50 g) and distilled water (600 g) were loaded in an autoclave (2-L, Hastelloy C) at room temperature. The autoclave was sealed and heated to 180° C. with agitation (200 rpm). After 125 h, the autoclave was cooled to room temperature. X-Ray powder diffraction indicated the material to be crystalline. The crystalline silica thus synthesized was then filtered, dried and calcined for 4 h at 550° C. The calcined silica (56 g) was analyzed to contain 5 ppm Al.

Background Comparative Experiment 2—Na,Pd-ZSM-5

A sample of Pd-containing ZSM-5 was prepared as follows:

A solution containing 1.5 g of $Na_2PdCl_6$, 35 g concentrated HCl, 30 g tetrapropylammonium bromide, and 410 g $H_2O$ was added to a solution containing 40 g of waterglass and 300 g $H_2O$. This mixture was placed in a polypropylene bottle and heated at 100° C. for 7 days. The resulting material was filtered, washed, and dried. The product was calcined in air by raising the temperature 50° C. per hour to 540° C. and heating the material at 540° C. for 10 hours.

Background Comparative Experiment 3—Pt-A

A sample of Pt-A zeolite was prepared as follows: A solution containing 40.5 g $NaAlO_2$, 75 g NaOH, 900 mL $H_2O$, and 0.100 g $(NH_3)_4PtCl_2.H_2O$ was added to a solution containing 31.8 g $Na_2SiO_3.5H_2O$, and 600 $H_2O$ at 90° C. The mixture was stirred until crystalline and then was filtered, washed, and dried.

Background Comparative Experiment 4—H,Pt-ZSM-5

A sample of H,Pt-ZSM-5 was prepared as follows. A solution containing 2 g $H_2PtCl_6$, 35 g concentrated HCl, 30 g tetrapropylammonium bromide, and 410 g of $H_2O$ was added to a solution containing 240 g of waterglass and 300 g $H_2O$. This mixture was placed in a polypropylene bottle, heated at 100° C. for 8 days, and then filtered, washed, and dried. The product was calcined in air by raising the temperature 50° C. per hour to 540° C. and heating the material at 540° C. for 10 hours. The calcined material was then contacted three times with a 10% $NH_4NO_3$ solution and filtered, washed, and dried. The product was then calcined in air by raising the temperature 50° C. per hour to 540° C. and heating the material at 540° C. for 10 hours.

Sample Conditions

Oxidation of CO, butane or maleic anhydride was carried out using a 2 mL u-tube reactor immersed in a sandbath where temperatures could be controlled. The reactor effluent was sampled on-line and analyzed with a GC thermal conductivity detector, after chromatographic separations in a Parapack column. Gas-flow conditions were kept constant and simulated actual gas ratios in the recirculating stream.

Three tests were run, composed of the following mixtures:

| Mixtures | Gas Flow Conditions |
|---|---|
| A. CO | 1.68 mL/minute |
| Helium | 121.6 mL/minute |
| Oxygen | 10.9 mL/minute |
| B. Butane | 0.66 mL/hr liquid |
| Helium | 121.6 mL/minute |
| Oxygen | 10.9 mL/minute |
| C. Maleic Anhydride 10% in $H_2O$ | 6.0 mL/hr liquid |
| Oxygen | 10.9 mL/minute |

The product stream was recorded and the percent of the initial CO, butane, or maleic anhydride converted to $CO_2$ over a particular catalyst was calculated from the concentrations in the effluent.

A. EXAMPLES 1-5/Pd/$SiO_2$

Catalysts were prepared by the techniques described above, and were then evaluated under the above described experimental conditions. The results given in Table I for samples of Pd/$SiO_2$ catalysts show that at Pd loadings of between approximately 0.00018 weight % (Example 2) and 0.00036 weight % (Example 3), 100% of the CO is converted to $CO_2$ with only 1 to 3% butane converted to $CO_2$. At higher loadings of Pd, significantly more butane is oxidized than at lower loadings of Pd, and at lower loadings of Pd than recommended, the CO is left either unreacted or only partially oxidized. At these preferred loadings of Pd (between 0.00018% and 0.00036% Pd), only 6-7% of maleic anhydride reacts with oxygen. That is comparable to the empty reactor. This inertness of the catalyst used toward maleic anhydride is traceable to the inert nature of the substrate as is evident from Table II where the preferred Pd/SiO$_2$ catalyst is compared to other substrates with and without metal. The more acidic substrates (e.g., zeolites of BCE2, BCE3, and BCE4) give significant decomposition of maleic anhydride. The preferred substrate to minimize maleic anhydride decomposition is one with low acidity such as silica gel.

B. EXAMPLES 6 & 7

EXAMPLE 6/V/P/O

The V/P/O catalyst (Background Experiment 16) was evaluated as a CO oxidation catalyst under the conditions described above. Essentially no CO$_2$ was observed in the exit stream.

EXAMPLE 7/Pd/V/P/O

The Pd/V/P/O (Background Experiment 17) was also evaluated and showed essentially total conversion of the CO to CO$_2$ with low butane oxidation to CO$_2$ and essentially no reaction of the maleic anhydride.

C. EXAMPLES 8 TO 12/Pt/SiO$_2$

Catalysts were prepared by the techniques described above, and were then evaluated under the above described experimental conditions.

The results given in Table III for samples of Pt/SiO$_2$ show that at Pt loadings of between greater than 0.0005% (Example 11) and less than 0.005% (Example 10) CO is totally converted to CO$_2$ and butane conversion is significantly less than 100%. At higher loadings of Pt, total conversion of CO to CO$_2$ is observed and total or near-total conversion of butane is assumed.

TABLE I

Effect of Pd Concentrations Pd/SiO$_2$ Series 410° C.

| Catalyst | Approx. % Pd | % Butane to CO$_2$ | % CO to CO$_2$ | % MA Reacted |
|---|---|---|---|---|
| Empty Reactor | — | 0 | 0 | 5 |
| Silica Gel | — | 0 | 0 | 8 |
| EXAMPLE 1 Pd/SiO$_2$ | 0.000016 | 0 | 25 | — |
| EXAMPLE 2 Pd/SiO$_2$ | 0.00018 | 1 | 100 | 6 |
| EXAMPLE 3 Pd/SiO$_2$ | 0.00036 | 3 | 100 | 7 |
| EXAMPLE 4 Pd/SiO$_2$ | 0.011 | 40 | 100 | — |
| EXAMPLE 5 Pd/SiO$_2$ | 0.11 | 60 | 100 | 50 |

TABLE II

Effect of Catalyst Acidity on Maleic Anhydride Decomposition

| Catalyst | Approx. wt. % Metal | Si/Al | * | ** | *** | **** |
|---|---|---|---|---|---|---|
| Empty Reactor | — | — | 5 | 0 | 5 | 0 |
| Silica Gel | — | — | 6 | 0 | 6 | 0 |
| Silicalite (BCE 1) | — | 300 | 18 | 0 | 18 | 0 |
| Na,Pd-ZSM-5 (BCE 2) | <0.1 | 50 | 0 | 0 | 95 | 5 |
| Pt-A (BCE 3) | — | 1 | 30 | 30 | 30 | 40 |
| H,Pt-ZSM-5 (BCE 4) | <0.1 | 50 | 22 | 55 | 35 | 10 |
| Pd/SiO$_2$ (EXAMPLE 3) | 0.00036 | — | 6 | 0 | 6 | 0 |

*% Maleic Anhydride Cleavage
**% Maleic Anhydride Decomposition to Acid Aldehyde
***% to CO$_2$
****% to Coke
BCE Background Comparative Experiment

TABLE III

Effect of Pt Concentrations for Pt/SiO$_2$ Series at 410° C.

| Catalyst | Approx. wt % Pt | % Butane to CO$_2$ | % CO to CO$_2$ |
|---|---|---|---|
| Empty Reactor | — | 0 | 0 |
| Silica Gel | — | 0 | 0 |
| EXAMPLE 8 Pt/SiO$_2$ (BE 6) | 0.1 | — | 100 |
| EXAMPLE 9 Pt/SiO$_2$ (BE 7) | 0.01 | — | 100 |
| EXAMPLE 10 Pt/SiO$_2$ (BE 8) | 0.005 | 68 | 100 |
| EXAMPLE 11 Pt/SiO$_2$ (BE 10) | 0.0005 | — | 32 |
| EXAMPLE 12 Pt/SiO$_2$ (BE 11) | 0.0001 | — | 13 |

Although preferred embodiments of the invention have been described herein, it is to be understood that there is no intent to limit the invention to the precise embodiments herein disclosed and it is to be further understood that the right is reserved to all changes and modifications coming within the scope of the invention defined in the appended claims.

What is claimed is:

1. A process for the selective oxidation of carbon monoxide, in the presence of a hydrocarbon mixture and/or a partially oxidized hydrocarbon mixture, comprising contacting the CO and the hydrocarbon and/or a partially oxidized hydrocarbon mixture with a catalyst comprising a metal selected from platinum and palladium loaded on a support selected from silica and polysilicic acid, the latter treated with vanadium and phosphorous oxide, in the presence of oxygen.

2. The process of claim 1 conducted at temperatures up to 500° C.

3. The process of claim 1 wherein the hydrocarbon and/or partially oxidized hydrocarbon mixture is composed of maleic anhydride, n-butane and other maleic anhydride precursors.

4. The process of claim 1 where the temperature is from 350° C. to 450° C.

5. The process of claim 4 in which the contact time between the carbon monoxide/hydrocarbon mixture and catalyst is from 0.1 to 15.0 seconds.

6. The process of claim 5 in which the contact time between the carbon monoxide/hydrocarbon mixture and catalyst is from 0.2–0.4 seconds.

7. The process of claim 6 wherein the oxidation of carbon monoxide is conducted in an excess of oxygen.

8. The process of claim 7 conducted at a pressure of 0.5 to 20 atmospheres.

9. The process of claim 8 carried out at a pressure of 2 to 4 atmospheres.

10. The process of claim 1 where the metal catalyst is palladium.

11. The process of claim 1 where the metal catalyst is platinum.

12. The process of claim 11 wherein the weight percent of platinum loaded on a support is between 0.0005 and 0.005 weight percent.

13. The process of claim 10 wherein the weight percent of palladium loaded on a support is between 0.00018 and 0.00036 weight percent.

14. The process of claim 1 wherein the process contains a partially oxidized hydrocarbon.

15. The process of claim 14 wherein the partially oxidized hydrocarbon is maleic anhydride.

16. The process of claim 1 wherein the metal is loaded on the inert support by an ion exchange process.

17. The process of claim 7 wherein the source of oxygen is air.

18. A process for the selective oxidation of carbon monoxide in the presence of a hydrocarbon mixture and/or a partially oxidized hydrocarbon mixture, said mixture containing butane and maleic anhydride, comprising contacting the carbon monoxide and the hydrocarbon and/or partially oxidized hydrocarbon mixture with a catalyst comprising Pd metal loaded on a support selected from silica and polysilicic acid, the latter treated with vanadium and phosphorous oxide, with a metal content greater than about $1.5 \times 10^{-4}$ wt. % but less than $4.0 \times 10^{-4}$ wt. %, in the presence of oxygen.

19. A process for the selective oxidation of carbon monoxide in the presence of a hydrocarbon mixture and/or a partially oxidized hydrocarbon mixture, said mixture containing butane and maleic anhydride, comprising contacting the carbon monoxide and the hydrocarbon and/or partially oxidized hydrocarbon mixture with a catalyst comprising Pt metal loaded on a support selected from silica and polysilicic acid, the latter treated with vanadium and phosphorous oxide, with a metal content between 0.005 wt. % and 0.0005 wt. %, in the presence of oxygen.

* * * * *